(12) United States Patent
Yamamoto

(10) Patent No.: US 9,161,896 B2
(45) Date of Patent: Oct. 20, 2015

(54) COSMETIC

(75) Inventor: Yumiko Yamamoto, Taito-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 13/978,148

(22) PCT Filed: Dec. 28, 2011

(86) PCT No.: PCT/JP2011/080486
§ 371 (c)(1),
(2), (4) Date: Jul. 3, 2013

(87) PCT Pub. No.: WO2012/093643
PCT Pub. Date: Jul. 12, 2012

(65) Prior Publication Data
US 2013/0303483 A1   Nov. 14, 2013

(30) Foreign Application Priority Data
Jan. 5, 2011   (JP) ................. 2011-000547

(51) Int. Cl.
| A61Q 19/00 | (2006.01) |
| A61K 8/68 | (2006.01) |
| A61K 8/58 | (2006.01) |
| A61K 8/63 | (2006.01) |
| A61K 8/44 | (2006.01) |
| A61K 8/19 | (2006.01) |

(52) U.S. Cl.
CPC . *A61K 8/585* (2013.01); *A61K 8/19* (2013.01); *A61K 8/44* (2013.01); *A61K 8/63* (2013.01); *A61K 8/68* (2013.01); *A61Q 19/00* (2013.01)

(58) Field of Classification Search
None
See application file for complete search history.

(56) References Cited

U.S. PATENT DOCUMENTS

| 5,372,814 | A | 12/1994 | Mizushima et al. | |
| 5,863,945 | A | 1/1999 | Murayama et al. | |
| 6,187,955 | B1 * | 2/2001 | Nagai et al. | 564/240 |
| 6,348,200 | B1 | 2/2002 | Nakajima et al. | |
| 2004/0122103 | A1 * | 6/2004 | Hoshino et al. | 514/616 |
| 2005/0152865 | A1 | 7/2005 | Yamamoto et al. | |
| 2005/0266065 | A1 | 12/2005 | Perrier et al. | |
| 2008/0045909 | A1 * | 2/2008 | Fossel | 604/290 |

FOREIGN PATENT DOCUMENTS

| CN | 1166135 A | 11/1997 |
| EP | 0 554 897 B1 | 9/1999 |
| JP | 5 213731 | 8/1993 |
| JP | 5 294989 | 11/1993 |
| JP | 8 225428 | 9/1996 |
| JP | 8 319263 | 12/1996 |
| JP | 9 165313 | 6/1997 |
| JP | 11 269054 | 10/1999 |
| JP | 2001 48721 | 2/2001 |
| JP | 2001 163758 | 6/2001 |
| JP | 2003 171269 | 6/2003 |
| WO | WO 97/14401 A1 | 4/1997 |

OTHER PUBLICATIONS

SciFinder, Sofcare Ceramide SLE structure, retrieved online on Oct. 22, 2014.*
International Search Report Issued Sep. 27, 2012 in PCT/JP11/080486 Filed Dec. 28, 2011.
Imokawa, G. et al., "A Possible Function of Structural Lipids in the Water-Holding Properties of the Stratum Corneum", The Journal of Investigative Dermatiology, vol. 84, No. 4, pp. 282-284, (1985).
Imokawa, G. et al., "Selective Recovery of Deranged Water-Holding Properties by Stratum Corneum Lipids", The Journal of Investigative Dermatiology, vol. 87, No. 6, pp. 758-761, (Dec. 1986).
Ismail M. Hafez et al., "Cholesteryl Hemisuccinate Exhibits pH Sensitive Polymorphic Phase Behavior", Biochimica et Biophysica Acta, 1463, 2000, pp. 107-114.

* cited by examiner

*Primary Examiner* — Jennifer A Berrios
(74) *Attorney, Agent, or Firm* — Oblon, McClelland, Maier & Neustadt, L.L.P.

(57) ABSTRACT

A cosmetic comprising the following components (A), (B), (C) and (D):
(A) 0.001 to 50% by weight of an organic acid represented by a general formula (1), wherein $R^1$ denotes a residue derived from a natural sterin having one hydroxy group or a hydrogenated product thereof, or a residue derived from bile acid in which the hydroxyl hydrogen atom is removed; $R^2$ denotes a divalent hydrocarbon group having 1 to 24 carbon atoms; and M denotes a hydrogen atom, an alkali metal, an alkaline earth metal, ammonium, alkanolammonium having 2 to 9 carbon atoms in total, alkylammonium or alkenylammonium having 1 to 22 carbon atoms in total, a pyridinium substituted with an alkyl group or an alkenyl group having 1 to 18 carbon atoms, or a basic amino acid;
(B) 0.001 to 20% by weight of a base;
(C) 0.0001 to 50% by weight of a ceramide; and
(D) water,
and comprising, as a component (E), an acid other than the component (A) in a content satisfying a relationship: $0 \leq (E)/(A) < 0.2$, and having pH of 6 to 11.

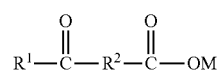

(1)

13 Claims, No Drawings

COSMETIC

CROSS REFERENCE TO RELATED APPLICATION

This application is a 371 of PCT/JP2011/080486, filed on Dec. 28, 2011, and claims priority to Japanese Patent Application No. 2011-000547, filed on Jan. 5, 2011.

FIELD OF THE INVENTION

The present invention relates to a cosmetic.

BACKGROUND OF THE INVENTION

A horny layer, which is present in the outermost layer of the skin, has a function of suppressing entering of substances from the outside and water evaporation from the inside of the skin, and, at the same time, holding moisture in the horny layer itself so as to keep softness or smooth appearance of the skin. Lipid called a horny intercellular lipid (hereinafter, referred to as a horny ICL) is present in spaces in the horny cells constituting the horny layer such that the lipid is filled in the spaces between the horny cells.

About 50% of lipid composition of the horny ICL is ceramides, and the remainder includes cholesterol, cholesterol ester, and fatty acid. In general, it is known that the reduction of the horny ICL, in particular, a ceramide causes not-preferable skin states such as rough skin, dry skin, and aged skin, and the horny layer reduced in a performance can be improved by externally supplementing the ceramide as a component for improving the function of the horny layer (Non-patent Literatures 1 and 2).

However, since the ceramide has a strong crystalline property, and a high melting point, it is difficult to stabilize the ceramide during formulation. Therefore, in order to blend stably the ceramide into skin external composition, a surfactant and a large amount of various oil agents, or the like, need to be used together, and as a result, it has not been possible to avoid deterioration of a feeling upon use and limitation of the nature of formulation.

Patent Literature 1 describes stabilization of the horny ICL containing a ceramide by using, for example, phospholipid and synthesized surfactants, but use of synthesized surfactants poses problems in terms of safety or a feeling upon use. Furthermore, there has been a problem that phospholipid itself is easily oxidized or degraded.

Furthermore, Patent Literature 2 describes that when a ceramide is emulsified with a sphingosine which is a lipid present in a horny ICL and an acid, the ceramide is not crystallized and can be retained stably. However, combination of the sphingosine and the acid shows cationic property, so that anionic substances cannot be coexistent.

On the other hand, an organic acid containing a sterol group is not the lipid which is present in the horny ICL, but has a similar structure to that of cholesterol sulfate or cholesteryl ester, and therefore has good affinity with the horny layer and high permeability.

CITATION LIST

Non-Patent Literatures

[Non-patent Literature 1] J. Invest. Dermatol., 84:282 (1985)
[Non-patent Literature 2] J. Invest. Dermatol., 87:758 (1986)

Patent Literatures

[Patent Literature 1] JP-A-2001-48721
[Patent Literature 2] JP-A-2003-171269

SUMMARY OF THE INVENTION

The present invention provides a cosmetic comprising the following components (A), (B), (C) and (D):
(A) 0.001 to 50% by weight of an organic acid represented by a general formula (1),

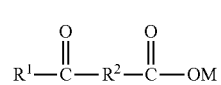

(1)

wherein $R^1$ denotes a residue derived from a natural sterin having one hydroxy group or a hydrogenated product thereof (hereinafter, referred to as a sterin), or a residue derived from bile acid in which the hydroxyl hydrogen atom is removed; $R^2$ denotes a divalent hydrocarbon group having 1 to 24 carbon atoms; and M denotes a hydrogen atom, an alkali metal, an alkaline earth metal, ammonium, alkanolammonium having 2 to 9 carbon atoms in total, alkylammonium or alkenylammonium having 1 to 22 carbon atoms in total, a pyridinium substituted with an alkyl group or an alkenyl group having 1 to 18 carbon atoms, or a basic amino acid;
(B) 0.001 to 20% by weight of a base;
(C) 0.0001 to 50% by weight of a ceramide; and
(D) water,
and comprising, as a component (E), an acid other than the component (A) in a content satisfying the relationship: $0 \leq (E)/(A) < 0.2$, and having pH of 6 to 11 as a composition.

Effects of the Invention

In a cosmetic of the present invention, a ceramide can be emulsified stably, and the cosmetic according to the present invention is excellent in stability, and has a high effect of improving rough skin. Furthermore, since it is stabilized with specific organic acid and base, it can coexist with an anionic substance.

EMBODIMENTS CARRYING OUT THE INVENTION

The present invention relates to a cosmetic in which a ceramide can be stably emulsified without crystallizing the ceramide and which has a high effect of improving roughness of the skin.

The present inventor has found that when a ceramide is emulsified with specific organic acid and base, the ceramide can be emulsified stably without crystallization, and further found that it is possible to stably retain a ceramide even if natural or synthetic surfactants, phospholipid, and the like, are not added, so that a cosmetic having excellent stability and a high effect of improving roughness of the skin can be obtained.

The organic acid of a component (A) used in the present invention is represented by the general formula (1).

In the general formula (1), examples of the natural sterin having one hydroxy group denoted by $R^1$ include cholesterol, stigmasterol, sitosterol, campesterol, lanosterol, ergosterol, and the like. Among them, cholesterol is preferable.

Furthermore, in the general formula (1), $R^2$ denotes a divalent hydrocarbon group having 1 to 24 carbon atoms and examples thereof include linear chain or branched chain alkylene group or alkenylene group, and groups represented by the following formulae are preferable:

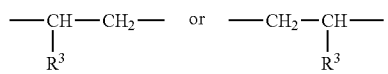

in the general formulae above, $R^3$ is a linear chain or branched chain alkyl group or alkenyl group having 6 to 20 carbon atoms (note here that in both formulae, a carboxyl group is bonded to the side chain at the right side).

Examples of $R^3$ include a 2-hexenyl group, a 2-octenyl group, a 2-decetel group, a 2-dodecenyl group, a 2-tetradecenyl group, a 2-hexadecenyl group, a 2 octadecenyl group, a 2-eicocenyl group, a hexyl group, an octyl group, a decyl group, a dodecyl group, a tetradecyl group, a hexadecyl group, an octadecyl group, and an eicosyl group, which are a linear chain or branched chain. Among them, a 2-tetradecenyl group, a 2-hexadecenyl group, a 2-octadecenyl group, a 2-eicocenyl group, a tetradecyl group, a hexadecyl group, an octadecyl group, and an eicosyl group are preferable.

Such organic acid (1) may be obtained by reacting a sterin with an alkenyl succinic acid anhydride or an alkyl succinic acid anhydride according to a method described in, for example, JP-A-H5-294989, and neutralizing them with alkaline substances if necessary.

One or two or more components (A) can be used, and the content thereof is 0.001 to 50% by weight, preferably 0.01 to 25% by weight, and more preferably 0.1 to 10% by weight with respect to the total composition. In this range, it is possible to obtain a cosmetic in which problems of a feeling on use, for example, stickiness are suppressed.

The component (A) can express a function like that of a surfactant in action with the below-mentioned component (B), and can stably emulsify a ceramide of the component (C) even if other surfactants are not contained. Thus, other surfactants for emulsifying the ceramide of the component (C) may not be contained.

The bases of the component (B) to be used in the present invention are not limited as long as they are water-soluble property, and they may be an organic base or an inorganic base.

As the organic base, one or two or more of organic bases selected from basic amino acids such as L-arginine, lysine and histidine; and alkanol amine such as monoethanolamine, diethanolamine, triethanolamine, aminomethyl propanol, aminomethyl propanediol, aminoethyl propanediol, and trishydroxy methyl aminoethane, are preferable. Furthermore, as the inorganic base, one or two or more of inorganic bases selected from sodium hydroxide and potassium hydroxide are preferable.

Among them, one or two or more selected from basic amino acids, sodium hydroxide, and potassium hydroxide are preferable, and furthermore, one or two or more selected from L-arginine, sodium hydroxide, and potassium hydroxide are more preferable.

The bases of the component (B) can be used in combination of one or two or more thereof, and the contents thereof is 0.001 to 20% by weight, preferably 0.01 to 5% by weight, and more preferably 0.01 to 3% by weight with respect to the total composition.

The component (B) neutralizes the component (A) to form a salt. Thereby, the component (A) can exhibit action like that of surfactants. Furthermore, it has a role for adjusting pH of the whole composition.

As the ceramide of the component (C) used in the present invention, one or two or more selected from compounds represented by the following general formula (2) or (3) are preferable.

(I) The compound represented by the general formula (2) may be a naturally derived ceramide or synthesized product thereof having the same structure.

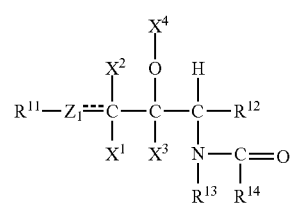

(In the general formula (2), $R^{11}$ denotes linear chain, branched chain or cyclic, and saturated or unsaturated hydrocarbon group having 7 to 19 carbon atoms, which is optionally substituted with a hydroxyl group; $Z_1$ denotes a methylene group or a methine group; $X^1$, $X^2$, and $X^3$ each independently denote a hydrogen atom, a hydroxyl group or an acetoxy group; $X^4$ denotes a hydrogen atom or forms an oxo group together with the neighboring oxygen atoms (wherein when $Z_1$ is a methine group, any one of $X^1$ and $X^2$ is a hydrogen atom, and the other is not present, and when $X^4$ forms an oxo group, $X^3$ is not present); $R^{12}$ denotes a hydroxymethyl group or an acetoxyl methyl group; $R^{13}$ denotes a hydrogen atom or an alkyl group having 1 to 4 carbon atoms; $R^{14}$ denotes a linear, branched or cyclic, and saturated or unsaturated hydrocarbon group having 5 to 30 carbon atoms, which is optionally substituted with a hydroxyl group, or a substituent in which a linear chain or branched chain, and saturated or unsaturated fatty acid having 8 to 22 carbon atoms, which is optionally substituted with a hydroxyl group, is ester-bonded to the ω-terminal of the alkyl group; and a broken line denotes it may be an unsaturated bond.)

Preferred is a compound in which $R^{11}$ is a linear chain alkyl group having 7 to 19 carbon atoms, and further preferably having 13 to 15 carbon atoms; and $R^{14}$ is a linear chain alkyl group having 9 to 27 carbon atoms which is optionally substituted with a hydroxyl group, or a linear chain alkyl group having 9 to 27 carbon atoms to which linoleic acid is ester-bonded. Furthermore, $X^4$ preferably denotes a hydrogen atom or forms an oxo group together with an oxygen atom. Preferable $R^{14}$ includes a tricosyl group, a 1-hydroxy pentadecyl group, a 1-hydroxy tricosyl group, a heptadecyl group, a 1-hydroxy undecyl group, and a nonacosyl group in which linoleic acid is ester-bonded to the ω-position.

The natural type ceramide is preferably one or two or more selected from ceramide Types 1 to 7 in which sphingosine, dihydrosphingosine, phytosphingosine, or sphingadienine is amidated (for example, ceramides of pig and human described in FIG. 2 of J. Lipid Res., 24: 759 (1983), and FIG. 4 of J. Lipid. Res., 35: 2069 (1994)).

Furthermore, N-alkyl products (for example, an N-methyl product) of them are included.

As such a ceramide, a natural type (D(-) product) optically-active substance, a non-natural type (L(+) product) optically-active substance, furthermore, a mixture of the natural type and the non-natural type, may be used. The relative configuration of the above-mentioned compound may be configuration of a natural type, and configuration of the other non-natural type, and further a configuration of a mixture thereof. Among them, one or two or more compounds selected from CERAMIDE1, CERAMIDE2, CERAMIDE3, CERAMIDE5, and CERAMIDE6II (all are described in INCI, 8th Edition) and compounds represented by the following formula are preferable.

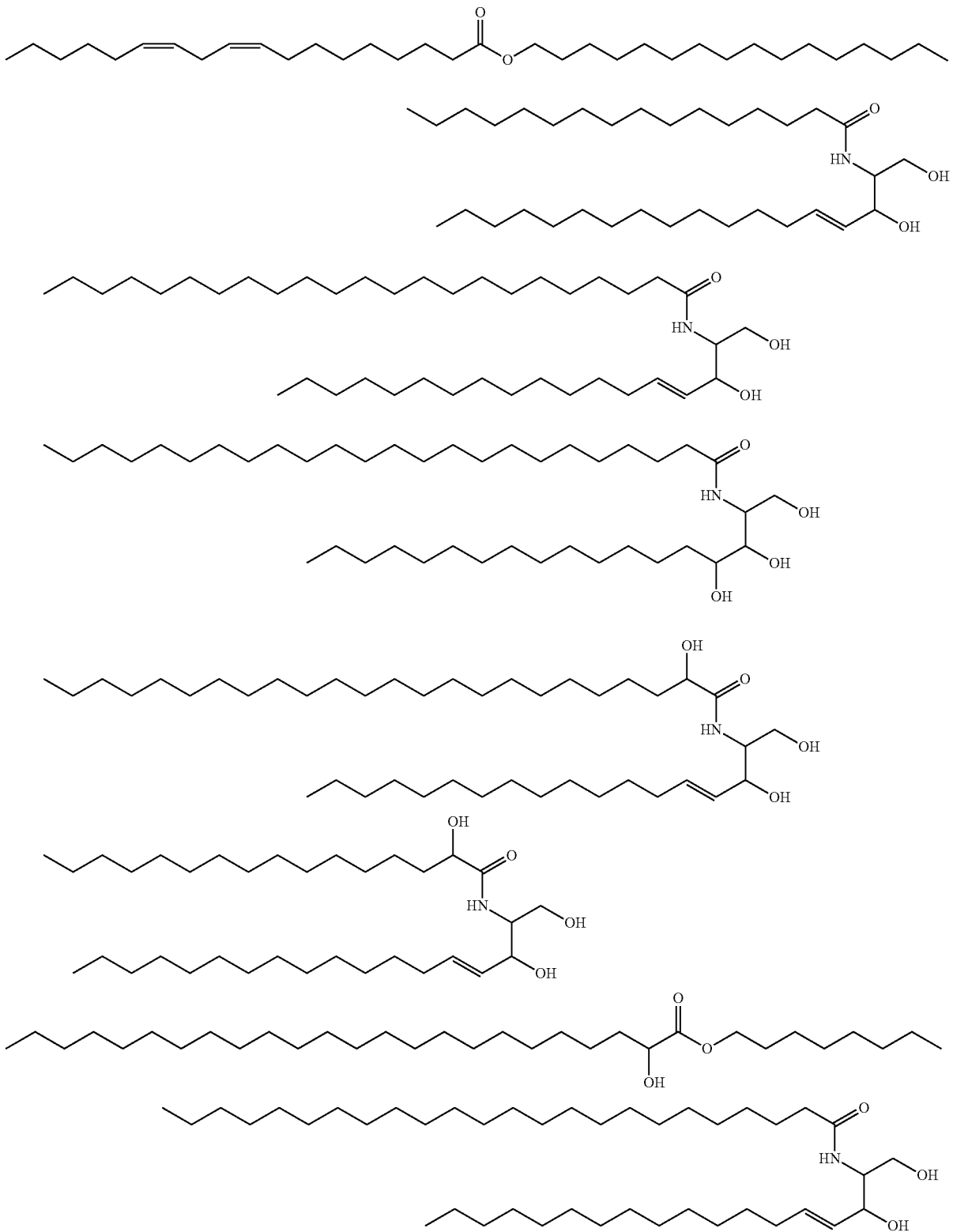

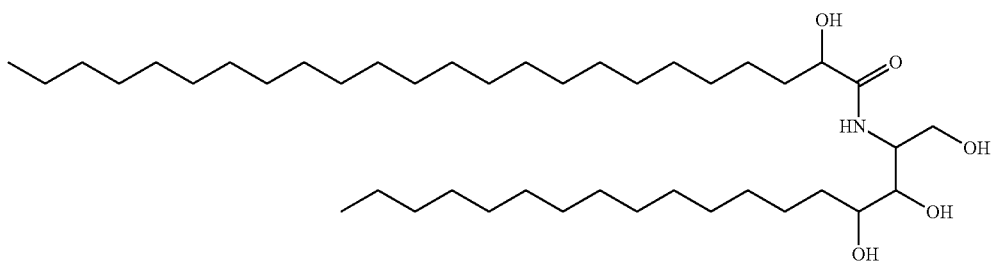 [SMILES: CCCCCCCCCCCCCCCCCCCCCCC(O)C(=O)NC(CO)C(O)C(O)CCCCCCCCCCCCCC]

These may be either a naturally extracted product or a synthesized product, and commercially available products can be used.

When such commercially available natural type ceramides are used, preferred are one or two or more selected from Ceramide I, Ceramide III, Ceramide IIIA, Ceramide IIIB, Ceramide IIIC, Ceramide VI (all manufactured by Cosmoferm Co., Ltd.), Ceramide TIC-001 (manufactured by TAKASAGO INTERNATIONAL CORPORATION), CERAMIDE II (manufactured by Quest International Co., Ltd.), DS-Ceramide VI, DS-CLA-Phytoceramide, C6-Phytoceramide, DS-ceramide Y3S (manufactured by DOOSAN Co., Ltd.), CERAMIDE2 (manufactured by Sederma Co., Ltd.).

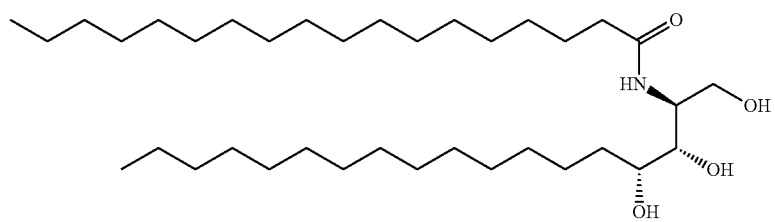
Ceramide III (manufactured by Cosmoferm Co., Ltd.)

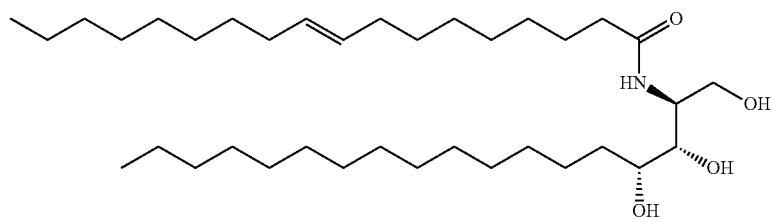
Ceramide IIIB (manufactured by Cosmoferm Co., Ltd.)

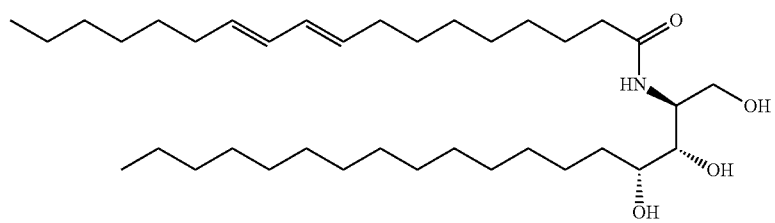
Ceramide IIIA (manufactured by Cosmoferm Co., Ltd.)

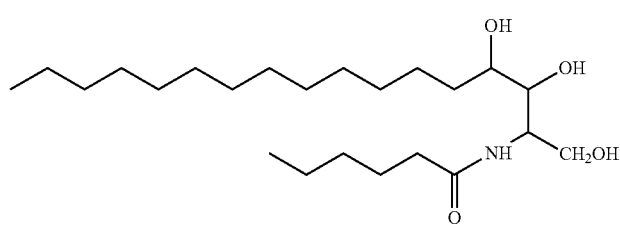
Phytoceramide (manufactured by DOOSAN Co., Ltd.)

-continued

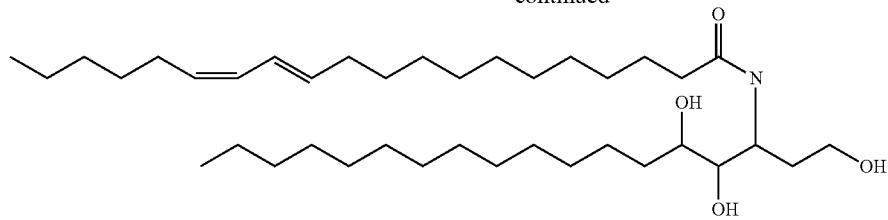
DS-CLA-Phytoceramide (manufactured by DOOSAN Co., Ltd.)

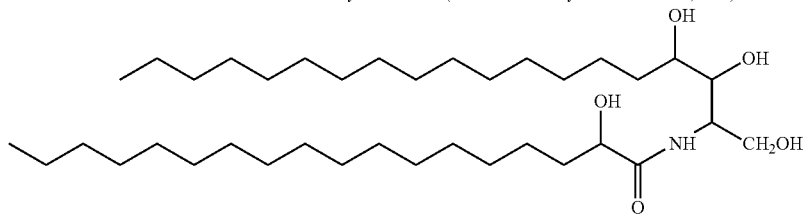
DS-Ceramide VI (manufactured by DOOSAN Co., Ltd.)

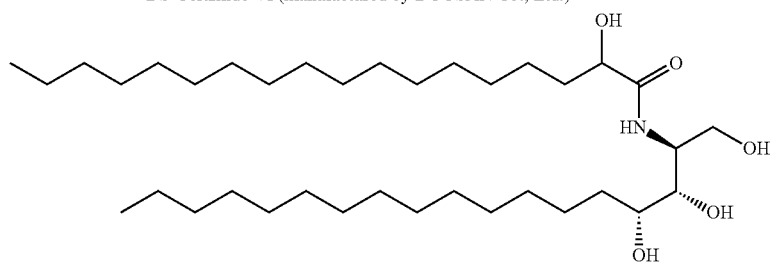
Ceramide VI (manufactured by Cosmoferm Co., Ltd.)

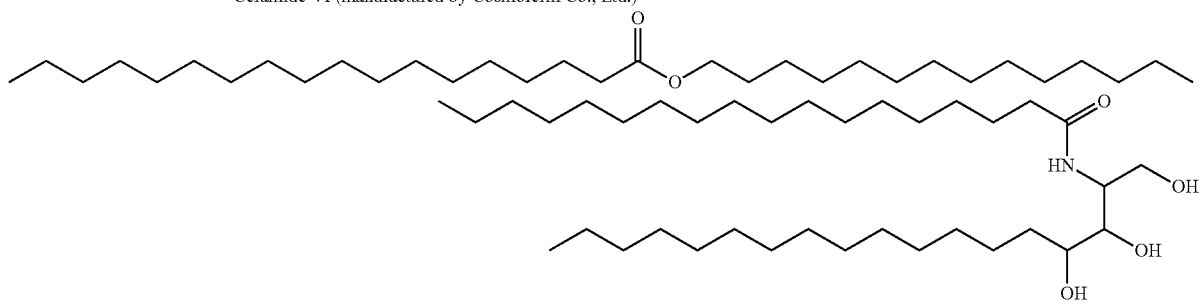
Ceramide I (manufactured by Cosmoferm Co., Ltd.)

(II) Pseudo type ceramide represented by the following general formula (3):

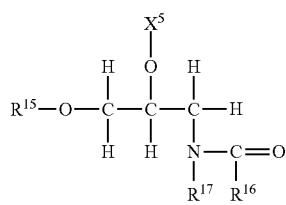
(3)

(In the general formula (3), $R^{15}$ denotes a linear chain, branched chain or cyclic, and saturated or unsaturated hydrocarbon group having 10 to 22 carbon atoms, which is optionally substituted with a hydroxyl group, or a hydrogen atom; $X^5$ denotes a hydrogen atom, an acetyl group or a glyceryl group; $R^{16}$ denotes a linear chain, branched chain or cyclic, and saturated or unsaturated hydrocarbon group having 5 to 22 carbon atoms, which is optionally substituted with a hydroxyl group or an amino group, or a substituent in which a linear chain or branched chain, and saturated or unsaturated fatty acid having 8 to 22 carbon atoms, which is optionally substituted with a hydroxyl group, is ester-bonded to the co-terminal of the hydrocarbon group; and $R^{17}$ denotes a hydrogen atom or an alkyl group having in total 1 to 30 carbon atoms, which is optionally substituted with a hydroxyl group, a hydroxyalkoxy group, an alkoxy group or an acetoxy group.)

$R^{16}$ is preferably a nonyl group, a tridecyl group, a pentadecyl group, an undecyl group in which linolic acid is ester-bonded to the ω-position, a pentadecyl group in which linolic acid is ester-bonded to the ω-position, a pentadecyl group in which 12-hydroxystearic acid is ester-bonded to the ω-position or an undecyl group in which methyl-branched isostearic acid is amide-bonded to the ω-position.

When $R^{15}$ is a hydrogen atom, $R^{17}$ is an alkyl group having in total 10 to 30 carbon atoms and preferably 12 to 20 carbon atoms, which is optionally substituted with a hydroxyl group, a hydroxyalkoxy group, an alkoxy group or an acetoxy group; when $R^{15}$ is a linear chain, branched chain or cyclic, and saturated or unsaturated hydrocarbon group having 10 to 22 carbon atoms, which is optionally substituted with a hydroxyl group, $R^{17}$ preferably denotes a hydrogen atom or an alkyl group having in total 1 to 8 carbon atoms, which is optionally substituted with a hydroxyl group, a hydroxyalkoxy group, an alkoxy group or an acetoxy group. Preferable hydroxyalkoxy group or alkoxy group of $R^{17}$ is a group having 1 to 7 carbon atoms.

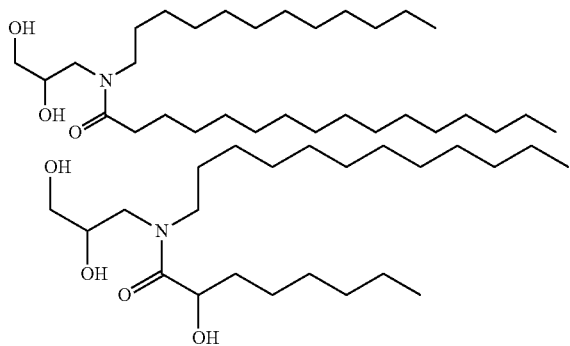

Preferred are the pseudo type ceramides represented by general formula (3) in which $R^{15}$ is a hexadecyl group, $X^5$ is a hydrogen atom, $R^{16}$ is a pentadecyl group, and $R^{17}$ is a hydroxyethyl group; in which $R^{15}$ is a hexadecyl group, $X^5$ is a hydrogen atom, $R^{16}$ is a nonyl group, and $R^{17}$ is a hydroxyethyl group; or in which $R^{15}$ is a hexadecyl group, $X^5$ is a glyceryl group, $R^{16}$ is a tridecyl group, and $R^{17}$ is a 3-methoxypropyl group. More preferred is the compound of general formula (3) in which $R^{15}$ is a hexadecyl group, $X^5$ is a hydrogen atom, $R^{16}$ is a pentadecyl group and $R^{17}$ is a hydroxyethyl group (N-(hexadecyloxy hydroxy propyl)-N-hydroxyethyl hexadecanamide).

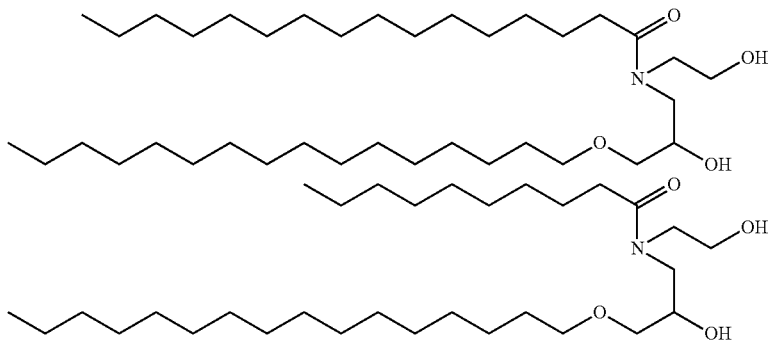

One or more of the ceramides of the component (C) can be used, and a content thereof in the total composition is 0.0001 to 50% by weight, preferably 0.001 to 20% by weight, more preferably 0.01 to 10% by weight, further preferably 0.1 to 8% by weight. It is preferable that the ceramides are contained in this range from the viewpoint that a moisturizing effect is efficiently provided to the skin, and that problems of a feeling upon use such as stickiness is suppressed.

Furthermore, a weight ratio of the component (A) to (C) preferably satisfies a relationship: $(A)/(C) \geq 0.001$, more preferably $(A)/(C) \geq 0.01$, and furthermore preferably $(A)/(C) \geq 0.1$ because crystallization of ceramides is suppressed, stable liquid crystal is formed and maintained. As a result, permeation into the skin can be promoted, and a water retaining amount can be improved. Furthermore, it is preferable to satisfy a relationship: $(A)/(C) \leq 100$ or less, and more preferably $(A)/(C) \leq 10$.

The content of the water in the component (D) to be used in the present invention in the total composition is 10 to 99% by weight, more preferably 40 to 95% by weight, and further preferably 40 to 88% by weight.

The cosmetic of the present invention may further contain, as the component (E), acids other than the component (A). Such acids are not limited as long as they can decrease pH of the cosmetic, and may be any of organic acid and inorganic acid.

Preferred organic acid includes one or two or more selected from monocarboxylic acids such as acetic acid, propionic acid, and butyric acid; dicarboxylic acids such as succinic acid, phthalic acid, fumaric acid, oxalic acid, malonic acid, and glutaric acid; oxycarboxylic acids such as glycolic acid, citric acid, lactic acid, pyruvic acid, malic acid, and tartaric acid; and amino acids such as glutamic acid and aspartic acid.

Furthermore, preferred inorganic acid includes one or two or more selected from hydrochloric acid, nitric acid, nitrous acid, sulfuric acid, sulfurous acid, phosphoric acid, phosphonic acid, and phosphinic acid.

Among them, the more preferable organic acid is dicarboxylic acid, and the more preferable inorganic acid is phosphonic acid.

It is preferable that the cosmetic of the present invention includes no component (E) or 0 to 1% by weight of the component (E) with respect to the total composition. The component (E) adjusts such that a composition emulsified by the components (A), (B), (C), and (D) has an appropriate pH. More specifically, since the composition emulsified by the components (A), (B), (C), and (D) has a high pH, the pH can be adjusted to an appropriate pH by adding the component (E).

The weight ratio of the component (E) to the component (A) satisfies a relationship: $0 \leq (E)/(A) < 0.2$, preferably $0 \leq (E)/(A) \leq 0.1$, and more preferably $0 \leq (E)/(A) \leq 0.08$ from the viewpoint of preventing reduction of the surface activity of the component (A) by salting out, and improving the water retaining amount of the skin. Furthermore, from the viewpoint of improving the long-term storage stability and the water retaining amount, the weight ratio preferably satisfies a relationship: $0 \leq (E)/(A) \leq 0.05$.

The cosmetic of the present invention may further include components to be used for general cosmetics, for example, oil ingredients, lower alcohol, water-soluble high molecules such as carboxyvinyl polymer, a moisturizing agent, an oxidation inhibitor, preservatives, a whitening agent, an ultraviolet absorber, vitamins, and other various ingredients with drug efficacy, powder, perfume, a coloring agent, and the like.

Furthermore, the cosmetic of the present invention includes preferably substantially no surfactants other than the above, and the content of the surfactants other than the above in the total composition is preferably 1.5% by weight or less, more preferably 1.0% by weight or less, further preferably 0.5% by weight or less, and more preferably 0.2% by weight or less from the viewpoint of low stimulation property.

Examples of the surfactants other than the above include nonionic surfactants and anionic surfactants. It is preferable that in the cosmetic of the present invention, cationic surfactants as the surfactants other than the above is not contained or 0.01% by mass or less of cationic surfactants is contained in the total composition from the viewpoint of stimulating property.

Examples of the nonionic surfactant include one or more selected from polyoxyalkylene sorbitan fatty acid ester, polyoxyalkylene sorbit fatty acid ester, polyoxyalkylene glycerine fatty acid ester, polyoxyalkylene fatty acid ester, polyoxyalkylene alkyl ether, polyoxyalkylene alkylphenyl ether, polyoxyalkylene (hydrogenated) castor oil, sucrose fatty acid ester, polyglycerine alkyl ether, polyglycerine fatty acid ester, fatty acid alkanolamide, and alkylglycoside.

The content of the nonionic surfactant in the total composition is preferably 1.0% by weight or less, more preferably 0.5% by weight or less, and further preferably 0.2% by weight or less from the viewpoint of reducing stimulation and improving a feeling upon use.

Examples of the anionic surfactants include one or more selected from fatty acid salt derived from fatty acid having 8 or more carbon atoms such as sodium laurate and potassium palmitate; alkyl sulfate ester salt such as sodium lauryl sulfate, potassium lauryl sulfate, and sodium stearyl sulfate; alkyl ether sulfate ester salt such as polyoxyethylene lauryl sulfate triethanolamine; N-acyl-sarcosine salt such as sodium lauroyl sarcosine; fatty acid amide sulfonate salt such as sodium N-myristoyl-N-methyl taurate; phosphate ester salt such as sodium monostearyl phosphate, sodium polyoxyethylene oleyl ether phosphate, and sodium polyoxyethylene stearyl ether phosphate; sulfosuccinate salt such as sodium di-2-ethylhexyl sulfosuccinate; alkylbenzensulfonate salt such as sodium linear dodecylbenzen sulfonate and triethanolamine lineardodecylbenzen sulfonate; N-acylglutamic acid salt such as monosodium N-lauroylglutamate, disodium N-stearoyl glutamate, and monosodium N-myristoyl-L-glutamate.

The content of the anionic surfactants in the total composition is preferably 0.5% by weight or less, more preferably 0.2% by weight or less, and further preferably 0.1% by weight or less from the viewpoint of reducing stimulation.

A method of producing a cosmetic of the present invention comprises mixing the components (A), (B), (C) and (D) while heating to a temperature not lower than the melting point of either the component (A) or the component (C), whichever is higher; and then cooling the mixture to 50° C. or less so as to obtain a cosmetic having pH 6 to 11. Furthermore, the method of producing the cosmetic of the present invention may further comprise adjusting a pH so as to adjust pH to 6 to 11 after cooling to 50° C. or less.

The step of mixing the components (A), (B), (C) and (D) preferably includes a step 1 of mixing the component (A), the component (B), and water (D1) which is a part of the component (D), and heating the mixture to a temperature not lower than the melting point of the component (A), and, after the step 1, includes a step 2 of mixing the component (C) and an oil phase containing other oil ingredients while heating the mixture to a temperature not lower than the highest melting point among all the components. In the step 2, after the component (C) is added, the other oil ingredients may be added.

Furthermore, the step of mixing the components (A), (B), (C) and (D) may include a step 1 of mixing the components (A) and (C) while heating the mixture to a temperature not lower than the melting point of either the component (A) or the component (C), whichever is higher, and, after the step 1, include a step 2 of adding a mixed solution of the component (B) and water (D1) which is a part of the component (D) and mixing them while heating. The step of adding the other oil ingredients may include a step of mixing the components while heating the mixture to a temperature not lower than the highest melting point of all the oil ingredients after the step 2.

The cosmetic of the present invention may further include polymers such as carboxyvinyl polymer, and a step 3 of adding a mixed solution of such polymers and water (D2) which is a part of the component (D) may be included after the step 2.

The pH adjusting step may be included in the step 3 by blending the component (E) into a part of water (D2) in the step 3 or may be carried out before or after the step 3. Adjustment of pH can be carried out by using the content of the component (B), but the pH adjusting step is a step of adding the component (E) and water which is a part of the component (D).

Furthermore, the method of producing the cosmetic of the present invention may further comprise a step of adding a water phase containing other water-soluble components and water (D3) which is a part of the component (D) and mixing them. A content of the component (D) is a total of the contents of the components (D1), (D2) and (D3).

The cosmetic of the present invention is produced as an oil-in-water emulsified cosmetic by carrying out a step of mixing the components (A), (B), (C) and (D) to be homogenized such that pH is preferably pH 7 or more while heating the mixture to a temperature not lower than the melting point of either the component (A) or the component (C), whichever is higher, more preferably pH 7.5 or more, and furthermore preferably pH 8 or more, as well as the pH is preferably pH 13 or less and more preferably pH 12 or less by, for example, adjusting the content of the component (B); then a step of cooling the mixed product to 50° C. or less; and then a step of adding the component (E) so as to adjust the pH to 6 to 11.

The cosmetic of the present invention has pH 6 to 11, preferably pH 6 to 8 from the viewpoint that the usability of the cosmetic is enhanced and stimulation is further reduced, and preferably pH 7 to 9 from the viewpoint that the water retaining amount in the skin is improved.

Note here that pH is directly measured at 25° C. without diluting each cosmetic by using COMPACT pH METER B-212 manufactured by HORIBA, Ltd.

<1> A cosmetic comprising following components (A), (B), (C) and (D):

(A) 0.001 to 50% by weight of an organic acid represented by a general formula (1):

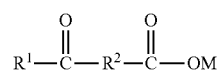

(1)

wherein $R^1$ denotes a residue derived from a natural sterin having one hydroxyl group or a hydrogenated product thereof, or a residue derived from bile acid in which the hydroxyl hydrogen atom is removed; and $R^2$ denotes a divalent hydrocarbon group having 1 to 24 carbon atoms; and M denotes a hydrogen atom, an alkali metal, an alkaline earth metal, ammonium, alkanolammonium having 2 to 9 carbon atoms in total, alkylammonium or alkenylammonium having 1 to 22 carbon atoms in total, a pyridinium substituted with an alkyl group or an alkenyl group having 1 to 18 carbon atoms, or a basic amino acid;

(B) 0.001 to 20% by weight of a base;

(C) 0.0001 to 50% by weight of a ceramide; and (D) water, and comprising, as a component (E), an acid other than the component (A) in a content satisfying a relationship: $0 \leq (E)/(A) < 0.2$, and having pH of 6 to 11.

<2> The cosmetic described in <1> in which the (C) ceramide is one or two or more selected from ones represented by the general formula (2) or (3):

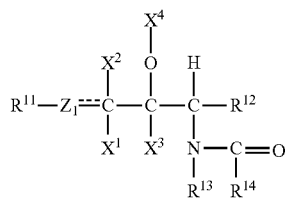

(2)

in the general formula (2), $R^{11}$ denotes a linear chain, branched chain or cyclic, and saturated or unsaturated hydrocarbon group having 7 to 19 carbon atoms, which is optionally substituted with a hydroxyl group; $Z_1$ denotes a methylene group or a methine group; $X^1$, $X^2$, and $X^3$ each independently denote a hydrogen atom, a hydroxyl group or an acetoxy group; $X^4$ denotes a hydrogen atom or forms an oxo group together with the neighboring oxygen atoms (wherein when $Z_1$ is a methine group, any one of $X^1$ and $X^2$ is a hydrogen atom and the other is not present, and when $X^4$ forms an oxo group, $X^3$ is not present); $R^{12}$ denotes a hydroxymethyl group or an acetoxymethyl group; $R^{13}$ denotes a hydrogen atom or an alkyl group having 1 to 4 carbon atoms; $R^{14}$ denotes a linear chain, branched chain or cyclic, and saturated or unsaturated hydrocarbon group having 5 to 30 carbon atoms, which is optionally substituted with a hydroxyl group, or a substituent in which a linear chain or branched chain, and saturated or unsaturated fatty acid having 8 to 22 carbon atoms, which is optionally substituted with a hydroxyl group, is ester-bonded to the ω-terminal of the alkyl group; and a broken line denotes it may be an unsaturated bond); and

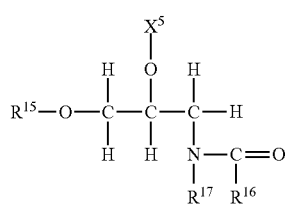

(3)

in the general formula (3), $R^{15}$ denotes a linear chain, branched chain or cyclic, and saturated or unsaturated hydrocarbon group having 10 to 22 carbon atoms, which is optionally substituted with a hydroxyl group or a hydrogen atom; $X^5$ denotes a hydrogen atom, an acetyl group or a glyceryl group; $R^{16}$ denotes a linear chain, branched chain or cyclic, and saturated or unsaturated hydrocarbon group having 5 to 22 carbon atoms, which is optionally substituted with a hydroxyl group or an amino group, or a substituent in which a linear chain or branched chain, and saturated or unsaturated fatty acid having 8 to 22 carbon atoms, which is optionally substituted with a hydroxyl group, is ester-bonded to the ω-terminal of the hydrocarbon group; and $R^{17}$ denotes a hydrogen atom or an alkyl group having in total 1 to 30 carbon atoms, which is optionally substituted with a hydroxyl group, a hydroxyalkoxy group, an alkoxy group or an acetoxy group).

<3> The cosmetic described in <1> or <2>, wherein a weight ratio of the components (A) to (C) satisfies a relationship: $(A)/(C) \geq 0.001$, preferably $100 \geq (A)/(C) \geq 0.01$, and more preferably $10 \geq (A)/(C) \geq 0.1$.

<4> The cosmetic described in any one of <1> to <3>, wherein the component (E) is an acid selected from the group consisting of dicarboxylic acid and phosphoric acid.

<5> The cosmetic described in any one of <1> to <4>, comprising 0.01 to 25% by weight, and preferably 0.1 to 10% by weight of the component (A).

<6> The cosmetic described in any one of <1> to <5>, comprising 0.01 to 5% by weight, and preferably 0.01 to 3% by weight of the component (B).

<7> The cosmetic described in any one of <1> to <6>, comprising 0.01 to 10% by weight, and preferably 0.1 to 8% by weight of the component (C).

<8> The cosmetic described in any one of <1> to <7>, wherein the component (B) is one or two or more selected from the group consisting of basic amino acids, alkanol amine, sodium hydroxide and potassium hydroxide, and preferably one or two or more selected from the group consisting of L-arginine, sodium hydroxide, and potassium hydroxide.

<9> The cosmetic described in any one of <1> to <8>, wherein a weight ratio of the components (E) to (A) satisfies a relationship: $0 \leq (E)/(A) \leq 0.1$, preferably $0 \leq (E)/(A) \leq 0.08$, and more preferably $0 \leq (E)/(A) \leq 0.05$.

<10> The cosmetic described in any one of <1> to <9>, wherein the content of surfactants other than salts of the component (A) is 1.5% by weight or less, preferably 1.0% by weight or less, more preferably 0.5% by weight or less, and further preferably 0.2% by weight or less, and more preferably the content of the anionic surfactants is 0.1% by weight or less.

<11> The cosmetic described in any one of <1> to <10>, which has a pH of from 6 to 8.

<12> The cosmetic described in any one of <1> to <10>, which has a pH of from 7 to 9.

<13> A method for producing a cosmetic described in any one of <1> to <12>, the method comprising: mixing the components (A), (B), (C) and (D) to be homogenized while heating the mixture to a temperature not lower than the melting point of either the component (A) or the component (C), whichever is higher, and then cooling to 50° C. or less.

<14> The method for producing a cosmetic described in <13>, comprising adjusting pH to 6 to 11 after cooling to 50° C. or less.

<15> The method for producing a cosmetic described in <13> or <14>, the method comprising mixing the components (A), (B), (C) and (D) to be homogenized such that pH is made to be pH 7 or more by adjusting a content of the component (B) while heating the mixture to a temperature not lower than the melting point of either the component (A) or the component (C), whichever is higher; after that, cooling to 50° C. or less; followed by adding the component (E) to adjust pH to 6 to 11.

<16> The method for producing a cosmetic described in any one of <13> to <15>, wherein the step of mixing the components (A), (B), (C) and (D) and heating them to be homogenized comprises a step 1 of heating and mixing the components (A) and (B) and a part of the component (D), and, after the step 1, comprises a step 2 of heating and mixing the component (C) and other oil ingredients.

<17> The method for producing a cosmetic described in any one of <13> to <15>, wherein the step of mixing and heating the components (A), (B), (C) and (D) to be homogenized comprises a step 1 of heating and mixing the components (A) and (C), and after the step 1, comprises a step 2 of heating and mixing the components (B) and a part of the component (D), and, after the step 2, comprises heating and mixing the other oil ingredients.

EXAMPLES

Examples 1 to 13 and Comparative Examples 1 to 4

Cosmetics having compositions shown in Tables 1 and 2 were produced and evaluated for the storage stability. The results are shown in Tables 1 and 2 together.
(Producing Method)
Components (A) and (C) were heated and stirred at 80 to 90° C. to be homogenized, and to the homogenized product, a component (B) which had been homogenized at 80° C. and 15% by weight of a component (D) were gradually added while stirring with a propeller at 450 rpm. Then, similarly, other oil ingredients were added thereto while stirring. The resultant product was cooled to 30° C. while further stirring to obtain a solution I. Next, methyl parahydroxybenzoate and glycerine were dissolved in 10% by weight of the component (D), and the resultant solution was added to the solution I to obtain a solution II. The pH of this condition was defined as pH at the time when the components (A) to (D) was dissolved and homogenized before the component (E) was added. Next, the component (E) and carboxyvinyl polymer were dissolved or dispersed in the rest of the component (D), and the resultant solution was added to the solution II to be homogenized. After that, the solution was cooled to 25° C. to obtain a cosmetic.
(Evaluation Method)
Each cosmetic was stored for one week at 50° C., 25° C. and −5° C., respectively, and then the appearance of the cosmetic was observed macroscopically. Furthermore, the cosmetic was observed under an optical microscope (400× magnification) for examining the presence or absence of precipitation of a crystal. As a result, cosmetics, in which neither emulsification separation nor precipitation of a crystal was recognized at any temperatures and which are excellent in stability, were evaluated as "A," and cosmetics, in which emulsification separation or precipitation of a crystal was recognized at any one of the temperatures and which were not stable, were evaluated as "B."

TABLE 1

| | component (% by weight) | Examples | | | | | | | |
|---|---|---|---|---|---|---|---|---|---|
| | | 1 | 2 | 3 | 4 | 5 | 6 | 7 | 8 |
| A | n-octadecenyl succinic acid cholesteryl monoester | 1 | 1 | 1 | 1 | 1 | 0.2 | | |
| | n-hexadecenyl succinic acid cholesteryl monoester | | | | 0.5 | | | 1 | 1 |
| | cholesterol hydrogen succinate | | | | | | | | |
| B | L-arginine | | | 0.2 | 0.2 | | | | |
| | potassium hydroxide | 0.034 | 0.054 | | | 0.2 | 0.036 | 0.054 | |
| | aminomethyl propanol | | | | | | | | 0.124 |
| E | phosphoric acid | | | | 0.01 | 0.01 | | | |
| | succinic acid | | | | | 0.03 | | | |
| C | N-(hexadecyloxy hydroxypropyl)-N-hydroxyethyl hexadecanamide | 1 | 1 | 1 | 3.5 | 1 | 2 | 1 | 1 |
| | ceramide (type 2) | | | | 0.5 | | | | |
| | squalane | | | | 3 | | | 1 | 1 |
| | dimethylpolysiloxane | | 2 | | 1 | | | | |
| | cholesterol | 0.5 | 0.5 | 1 | | 0.5 | 0.5 | 1 | 1 |
| | cetanol | | | | 1 | | | | |
| | cholesteryl isostearate | | | | 1 | | | | |
| | glycerine | 10 | 10 | 10 | 10 | 10 | 5 | 10 | 10 |
| | carboxyvinyl polymer | | 0.1 | 0.01 | | 0.1 | 0.1 | 0.08 | 0.1 |
| | methyl parahydroxybenzoate | 0.1 | 0.1 | 0.1 | 0.1 | 0.1 | 0.1 | 0.1 | 0.1 |
| D | ion exchanged water | balance | balance | balance | balance | balance | balance | balance | balance |
| | Total | 100 | 100 | 100 | 100 | 100 | 100 | 100 | 100 |
| | pH: when dissolved and homogenized (when components (A), (B), (C) and (D) are mixed) | 8.5 | 9.2 | 8.4 | 8.4 | 12.2 | 11.4 | 9.2 | 9.6 |
| | immediately after manufactured (pH as cosmetic) | 8.5 | 6.4 | 6.6 | 6.8 | 9.4 | 6.9 | 6.4 | 7.6 |
| | E/A | 0 | 0 | 0.01 | 0.01 | 0.03 | 0 | 0 | 0 |
| | A/C | 1 | 1 | 1 | 0.375 | 1 | 0.1 | 1 | 1 |
| | storage stability | A | A | A | A | A | A | A | A |

TABLE 2

| | component (% by weight) | Examples | | | | | Comparative Examples | | | |
|---|---|---|---|---|---|---|---|---|---|---|
| | | 9 | 10 | 11 | 12 | 13 | 1 | 2 | 3 | 4 |
| A | n-octadecenyl succinic acid cholesteryl monoester | | | | 1 | | 1 | 0.0001 | 1 | 1 |
| | n-hexadecenyl succinic acid cholesteryl monoester | | 7 | 1 | | 7 | | | | |
| | cholesterol hydrogen succinate | 1 | | | | | | | | |
| B | L-arginine | | 2 | | 0.2 | 1.4 | | | 0.2 | |
| | potassium hydroxide | 0.054 | | 0.2 | | | 0.054 | | | 0.2 |
| | aminomethyl propanol | | | | | | | | | |
| E | phosphoric acid | | | | 0.01 | | | | 0.02 | |
| | succinic acid | | | 0.08 | | | | | | 0.2 |

TABLE 2-continued

| | component (% by weight) | Examples 9 | 10 | 11 | 12 | 13 | Comparative Examples 1 | 2 | 3 | 4 |
|---|---|---|---|---|---|---|---|---|---|---|
| C | N-(hexadecyloxy hydroxypropyl)-N-hydroxyethyl hexadecanamide (type 2) | 1 | 0.1 | 1 | 1 | 7 | 1 | 1 | 1 | 1 |
| | squalane | | | | 1 | | | | 1 | |
| | dimethylpolysiloxane | | | | | | | | | |
| | cholesterol | 0.5 | | | 1 | | 0.5 | 0.5 | 1 | 0.5 |
| | cetanol | | | | | | | | | |
| | cholesteryl isostearate | | | | | | | | | |
| | glycerine | 10 | 5 | 10 | 10 | 5 | 10 | 10 | 10 | 10 |
| | carboxyvinyl polymer | 0.1 | | | | | | 0.1 | | 0.1 |
| | methyl parahydroxybenzoate | 0.1 | 0.1 | 0.1 | 0.1 | 0.1 | 0.1 | 0.1 | 0.1 | 0.1 |
| D | ion exchanged water | balance | balance | balance | balance | balance | balance | balance | balance | balance |
| | Total | 100 | 100 | 100 | 100 | 100 | 100 | 100 | 100 | 100 |
| | pH: when dissolved and homogenized (when components (A), (B), (C) and (D) are mixed) | 7.6 | 9.3 | 11.9 | 8.4 | 7.9 | 6.8 | 11.1 | 8.4 | 12 |
| | immediately after manufactured (pH as cosmetic) | 6.1 | 9.3 | 11.0 | 6.6 | 7.9 | 6.8 | 7.2 | 4 | 7.1 |
| | E/A | 0 | 0 | 0.08 | 0.01 | 0 | 0 | 0 | 0.02 | 0.2 |
| | A/C | 1 | 70 | 1 | 1 | 1 | 1 | 0.0001 | 1 | 1 |
| | storage stability | A | A | A | A | A | B | B | B | B |

From the results of Tables 1 and 2, all of the cosmetics of the present invention were excellent in the storage stability. Furthermore, when the cosmetics of these Examples were applied to the skin, they exhibited excellent permeability to the skin and excellent effect of improving roughness of the skin.

Test Example

Among the cosmetics of the Examples and Comparative Examples, cosmetic shown in Table 3 were evaluated for the water retaining amount. Results thereof are also shown in Table 3.
(Evaluation Method)

The measurement of the moisture amount of the skin was conducted at four portions in the vicinity each of three regions in the antebrachium, 12 portions in total, by using Corneometer (CORNEOMETER CM825, manufactured by Integral Corporation), and numeric values displayed on the Corneometer were used as the moisture amounts. Firstly, the moisture amount of the skin measured 10 minutes after the antebrachium had been washed with facial cleanser (Biore Cleansing Foam manufactured by KAO CORPORATION) and the water content had been removed was defied as an initial value. Next, each cosmetic was applied, the moisture amount of the skin was measured 6.5 hours after the application without washing, and the numeric value obtained by subtracting the initial value from the measured value was defined as the water retaining amount. Furthermore, after washing in the morning and after taking a bath, each cosmetic was applied, and then the moisture amount was measured 24 hours after the application without washing, and the numeric value obtained by subtracting the initial value from the measured value was defined as a water retaining amount of "24 hours after the application without washing." Similarly, the moisture amount was measured after washing before measurement 24 hours after the application, and the numeric value obtained by subtracting the initial value from the measured value was defined as a water retaining amount of "24 hours after the application after washing."

TABLE 3

| | component (% by weight) | Examples 5 | 7 | 12 | Comparative Examples 3 |
|---|---|---|---|---|---|
| A | n-octadecenyl succinic acid cholesteryl monoester | 1 | | 1 | 1 |
| | n-hexadecenyl succinic acid cholesteryl monoester | | 1 | | |
| B | L-arginine | | | 0.2 | 0.2 |
| | potassium hydroxide | 0.2 | 0.054 | | |
| E | phosphoric acid | | | 0.01 | 0.02 |
| | succinic acid | 0.03 | | | |
| C | N-(hexadecyloxy hydroxypropyl)-N-hydroxyethyl hexadecanamide | 1 | 1 | 1 | 1 |
| | squalane | | 1 | 1 | 1 |
| | cholesterol | 0.5 | 1 | 1 | 1 |
| | glycerine | 10 | 10 | 10 | 10 |
| | carboxyvinyl polymer | 0.1 | 0.08 | | |
| | methyl parahydroxybenzoate | 0.1 | 0.1 | 0.1 | 0.1 |
| D | ion exchanged water | balance | balance | balance | balance |
| Total | | 100 | 100 | 100 | 100 |
| pH: | when dissolved and homogenized (when components (A), (B), (C) and (D) are mixed) | 12.2 | 9.2 | 8.4 | 8.4 |
| | immediately after manufactured (pH as cosmetic) | 9.4 | 6.4 | 6.6 | 4 |

TABLE 3-continued

| component (% by weight) | Examples | | | Comparative Examples |
| --- | --- | --- | --- | --- |
| | 5 | 7 | 12 | 3 |
| E/A | 0.03 | 0 | 0.01 | 0.02 |
| A/C | 1 | 1 | 1 | 1 |
| water retaining amount (6.5 hours after the application without washing) | 14.0 | 19.7 | 21.8 | 10.0 |
| water retaining amount (24 hours after the application without washing) | 25.4 | 34.5 | 16.5 | 7.6 |
| water retaining amount (24 hours after the application after washing) | 16.4 | 12.5 | 10.5 | −0.3 |

As shown in Table 3, in both cases 6.5 hours and 24 hours after the application, higher resultant values of the water retaining amount were obtained in Examples as compared with Comparative Example. Furthermore, Examples 5 and 7 showed extremely high values of the water content maintaining amount 24 hours after the application before washing, and it is thought that the cosmetics remain in the skin also 24 hours after the application. Furthermore, 24 hours after the application and after washing, Examples showed high results of the water retaining amount and it is thought that the permeability to the skin is high.

The invention claimed is:

1. A cosmetic comprising the following components (A), (B), (C) and (D), and (E):
   (A) 0.1-7% by weight of an organic acid selected from the group consisting of n-octadecenyl succinic acid cholesteryl monoester, n-hexadecenyl succinic acid cholesteryl monoester, cholesterol hydrogen succinate and mixtures thereof;
   (B) 0.01-3% by weight of a base;
   (C) 0.1-8% by weight of a ceramide;
   (D) water; and
   optionally, (E), an acid other than the component (A), wherein
   a weight ratio of the component (E) to (A) satisfies:

$0 \leq (E)/(A) \leq 0.1$, and the cosmetic has a pH of 6 to 11.

2. The cosmetic according to claim 1, wherein a weight ratio of the components (A) to (C) satisfies: $(A)/(C) \geq 0.001$.

3. The cosmetic according to claim 1, wherein the component (B) is at least one member selected from the group consisting of a basic amino acid, an alkanol amine, sodium hydroxide and potassium hydroxide.

4. The cosmetic according to claim 1, wherein the ceramide of component (C) is at least one member selected from the group consisting of a compound represented by formula (2) or (3):

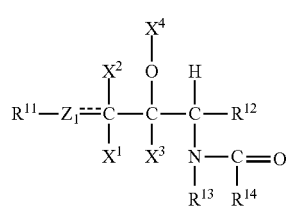

(2)

wherein $R^{11}$ represents linear chain, branched chain or cyclic, and saturated or unsaturated hydrocarbon group having 7 to 19 carbon atoms, which is optionally substituted with a hydroxyl group; $Z^1$ represents a methylene group or a methine group; $X^1$, $X^2$ and $X^3$ each independently represent a hydrogen atom, a hydroxyl group or an acetoxy group; $X^4$ represents a hydrogen atom or forms an oxo group together with the neighboring oxygen atoms; wherein when $Z^1$ is a methine group, any one of $X^1$ and $X^2$ is a hydrogen atom, and the other is not present, and when $X^4$ forms an oxo group, $X^3$ is not present; $R^{12}$ represents a hydroxymethyl group or an acetoxyl methyl group; $R^{13}$ represents a hydrogen atom or an alkyl group having 1 to 4 carbon atoms; $R^{14}$ represents a linear, branched or cyclic, and saturated or unsaturated hydrocarbon group having 5 to 30 carbon atoms, which is optionally substituted with a hydroxyl group, or a substituent in which a linear chain or branched chain, and saturated or unsaturated fatty acid having 8 to 22 carbon atoms, which is optionally substituted with a hydroxyl group, is ester-bonded to the ω-terminal of the alkyl group; and a broken line denotes it may be an unsaturated bond;

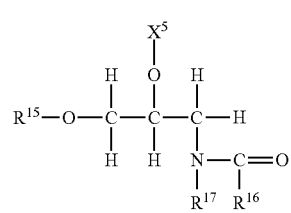

(3)

wherein $R^{15}$ represents a linear chain, branched chain or cyclic, and saturated or unsaturated hydrocarbon group having 10 to 22 carbon atoms, which is optionally substituted with a hydroxyl group, or a hydrogen atom; $X^5$ represents a hydrogen atom, an acetyl group or a glyceryl group; $R^{16}$ represents a linear chain, branched chain or cyclic, and saturated or unsaturated hydrocarbon group having 5 to 22 carbon atoms, which is optionally substituted with a hydroxyl group or an amino group, or a substituent in which a linear chain or branched chain, and saturated or unsaturated fatty acid having 8 to 22 carbon atoms, which is optionally substituted with a hydroxyl group, is ester-bonded to the ω-terminal of the hydrocarbon group; and $R^{17}$ denotes a hydrogen atom or an alkyl group having in total 1 to 30 carbon atoms, which is optionally substituted with a hydroxyl group, a hydroxyalkoxy group, an alkoxy group or an acetoxy group.

5. The cosmetic according to claim 1, wherein a weight ratio of the component (A) to (C) satisfies: $0.1 \leq (A)/(C) \leq 10$.

6. The cosmetic according to claim 1, further comprising a content of surfactants other than component (A) in an amount of 0.2% by weight or less.

7. A method for producing the cosmetic according to claim 1, the method comprising:
mixing components (A), (B), (C) and (D) to be homogenized while heating the mixture to a temperature not lower than the melting point of either the component (A) or the component (C), whichever is higher, and then cooling to 50° C. or less, followed by adjusting pH to 6 to 11.

8. A method for producing the cosmetic according to claim 1, the method comprising:
mixing components (A), (B), (C) and (D) to be homogenized such that a content of the component (B) is adjusted to be pH 7 or more while heating the mixture to a temperature not lower than the melting point of either the component (A) or the component (C), whichever is higher, and then
cooling to 50° C. or less, followed by
adding the component (E) so as to adjust pH to 6 to 11.

9. The method according to claim 7, wherein said mixing of components (A), (B), (C) and (D) comprises:
mixing the component (A), the component (B), and a part of the component (D), and heating the mixture to a temperature not lower than the melting point of the component (A); and thereafter
mixing the component (C) and an oil phase containing other oil ingredients while heating the mixture to a temperature not lower than the highest melting point among all the components.

10. The method according to claim 7, wherein said mixing of components (A), (B), (C) and (D) comprises:
mixing the components (A) and (C) while heating the mixture to a temperature not lower than the melting point of either the component (A) or the component (C), whichever is higher;
thereafter adding a mixed solution of the component (B) and a part of the component (D) and mixing them while heating; and thereafter adding other oil ingredients.

11. A method for using the cosmetic according to claim 1, comprising applying the cosmetic on skin.

12. The cosmetic according to claim 1, comprising (E), the acid other than the component (A), wherein
the weight ratio of the components (E) to (A) satisfies:

$0 < (E)/(A) \leq 0.1$.

13. The cosmetic according to claim 12, wherein the component (E) is an acid selected from the group consisting of dicarboxylic acid and phosphoric acid.

* * * * *